United States Patent [19]

Esanu et al.

[11] Patent Number: 5,047,537

[45] Date of Patent: Sep. 10, 1991

[54] SEPARATION OF ISOMERS OF FURO (3,4-C) PYRIDINE DERIVATIVES

[75] Inventors: Andre Esanu, Paris, France; Charles Eck, Shrewsbury, Mass.

[73] Assignee: Societe de Conseils de Recherches et d'Applications Scientifiques (S.C.R.A.S.), France

[21] Appl. No.: 598,653

[22] PCT Filed: Apr. 2, 1990

[86] PCT No.: PCT/FR90/00228

§ 371 Date: Oct. 18, 1990

§ 102(e) Date: Oct. 18, 1990

[30] Foreign Application Priority Data

Apr. 3, 1989 [GB] United Kingdom ............... 8907480

[51] Int. Cl.[5] ........................................... C07D 491/48
[52] U.S. Cl. .................................................. 546/116
[58] Field of Search ...................................... 546/116

[56] References Cited

FOREIGN PATENT DOCUMENTS 0157384 10/1985 European Pat. Off. .
0337858 10/1989 European Pat. Off. .
 779318  7/1957 United Kingdom .
2092586  8/1982 United Kingdom .

OTHER PUBLICATIONS

Lubineau et al., Tet. Letters, 26(14), pp. 1713–1716 (1985).
Gerding et al., HRC CC, J. High Resolution Chromatogr., Chromatogr. Commun., 10 (9), pp. 523–525, (1987), Chem. Abstracts, vol. 108, 119057n (1987).

Primary Examiner—Bernard Dentz
Attorney, Agent, or Firm—Lucas & Just

[57] ABSTRACT

This invention relates to a method for the separation of stereoisomers of 7-hydroxy-furo[3,4-c]pyridine derivatives of the formula

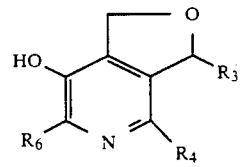

wherein $R_3$, $R_4$ and $R_6$ represent various substitutents, which comprises reacting a fully O-acetylated monosaccharide halogenide with a racemate of the selected 7-hydroxy-furo[3,4-c]pyridine derivative, to form the (+) and (−) (O-acetylated monosaccharide) (furo[3,4-c] pyridine 7-yl derivative) ethers, then separating the (+) and the (−) ethers by selective crystallization, in an hydroalcoholic medium, either of the acetylated forms or of the corresponding desacetylated forms and, finally, working up each of the separated derivatives by the usual routes. The compounds are known pharmaceuticals.

5 Claims, No Drawings

SEPARATION OF ISOMERS OF FURO (3,4-C) PYRIDINE DERIVATIVES

The invention relates to a method for the separation of stereoisomers of furo[3,4-c]pyridine derivatives.

Furo[3,4-c]pyridine derivatives of the general formula I

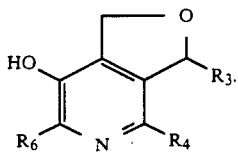

I wherein $R_3$ represents a hydrogen atom, a straight chain saturated hydrocarbon group having from 1 to 5 carbon atoms or unsaturated hydrocarbon group having from 2 to 5 carbon atoms, a heterocyclic group having up to 6 ring atoms, a phenyl group, a phenylalkyl or phenylalkenyl group, said groups being optionally substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α or β-alkoxy-N-pyrrolidinyl groups in which the alkoxy group has from 1 to 5 carbon atoms; $R_4$ represents a hydrogen or chlorine atom and $R_6$ represents a lower saturated or unsaturated hydrocarbon group up to $C_5$, optionally substituted by a hydroxy radical, by a amino rest $N(R)_2$ wherein R stands for hydrogen or a lower alkyl up to $C_3$. These compounds are known under their racemic form, for instance by our U. S. patent application Ser. Nos. 4,383,998, 4,585,776, 4,569,938, 4,569,939 and 4,581,362. They have various therapeutical activities, but it has been found that, for most of them, one stereoisomer is more active than the other. It is thus desirable to devise a method for the separation of their stereoisomers.

The invention provides a method for the separation of stereoisomers of 7-hydroxy-furo[3,4-c]pyridine derivatives which comprises reacting a fully O-acetylated monosaccharide halogenide with a racemate of the selected 7-hydroxy-furo[3,4-c]pyridine derivative, to form the (+) and (−) (O-acetylated monosaccharide) (furo[3,4-c]pyridine 7-yl derivative) ethers, then separating the (+) and the (−) ethers by selective crystallization, in an hydroalcoholic medium, either of the acetylated forms or of the corresponding desacetylated forms and, finally, working up each of the separated derivatives, optionally hydrolysing the ester function, and breaking the ether bond between monosaccharide and furo[3,4-c]pyridine derivative. The desacetylation is to be carried out before the selective crystallization when the desacetylated derivatives show a greater difference of solubility in the hydroalcoholic medium compared to the acetylated ones. The term monosaccharide is intended for a glucuronate ester or a glycoside; the term O-acetylated monosaccharide halogenide represents a bromide or a chloride of the said monosaccharide wherein all the hydroxy groups are acetylated. The hydroalcoholic medium used for the selective crystallisation of the present invention consists of aqueous solution of a lower alkanol selected from the group consisting of methanol, ethanol and the propanols.

EXAMPLE 1

This example describes the separation of the stereoisomers of 1,3-dihydro-6-methyl-3-(p-chloro)phenyl-furo[3,4-c]pyridine.

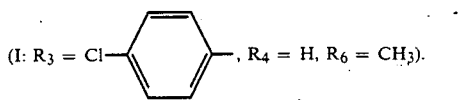

(I: $R_3$ = Cl-⟨phenyl⟩-, $R_4$ = H, $R_6$ = $CH_3$).

REACTION NO. 1

Synthesis of
(+)-1,3-dihydro-6-methyl-3-p-chlorophenylfuro[3,4-c]pyridine 7-O-(β-D-glucuronate) methyl ester triacetate and
(-)-1,3-dihydro-6-methyl-3-p-chlorophenylfuro[3,4-c]pyridine 7-O-(β D-glucuronate) methyl ester triacetate.

4.06 g (0.015 mole) of 1,3-dihydro-6-methyl-3-p-chlorophenyl-7-hydroxy-furo[3,4-c]pyridine free base, 1.13 g (4 mmole) of mercuric chloride and 6.75 g of molecular sieve (4 Å) were suspended in 85 ml of 1,2-dichloroethane, and refluxed for 15 minutes. 8.18 g (0.020 mole) of methyl (tri-O-acetyl-α-D-glucopyranosyl bromide)-uronate was then added in one portion and refluxing was continued under nitrogen for 15 hours. After cooling, the solvent was decanted into a separatory funnel, and the flask/sieves were rinsed five times with 50 ml aliquots of methylene dichloride. The organic layers were combined, and extracted 3 times with 75 ml aliquots of 10% potassium iodide solution, 3 times with some aliquots of 5% sodium bicarbonate solution and twice with 30 ml aliquots of saturated sodium chloride solution. After drying on anhydrous magnesium sulphate, the solution was filtered and the filtrate was stripped to dryness on a rotary evaporator. The crude residue (7.5 g) was dissolved in 150 ml of methanol.

On standing at room temperature, two crops of a fluffy white solid (2.26 g) were collected. The filtrate was concentrated to 20 ml, provided on cooling a second solid which was recrystallized from methanol. Filtration provided 1.6 g of a crystalline white solid (yield = 44.5%).

Based on spectroscopic evaluation, the first solid was determined to be the (−)methyl ester tri-acetate and the second solid the (+)methyl ester tri-acetate.

Analysis for (+)compound calculated for $C_{27}H_{28}ClNO_{11}$, C=56.11%, H=4.88%, N=2.42%, observed: C=55.90%, H=4.80%, N=2.64%, $^1$H NMR in $CDCl_3$, 2.03 ppm (3H, s), 2.05 ppm (3H, s), 2.13 ppm (3H, s), 2.49 ppm (3H, s), 3.75 ppm (3H, s); $^{13}$C NMR in $CDCl_3$, 18.7 ppm ($CH_3$), 20.42 ppm ($CH_3$), 52.77 ppm (O-$CH_3$), 101.0 ppm (C-1'); (C=0.41 in $CHCl_3$) HPLC, $R_T$=10.88 minn. (98.0%), m.p. 230°–231° C.

REACTION NO. 2

Synthesis of desacetylated form of (−)methyl ester compound of reaction 1

0.5 g (0.8 mmole) of the (−)methyl ester tri-acetate obtained in reaction No. 1 was dissolved in 5 ml of 1.5N methanolic hydrogen chloride. The solution was placed in a 25 ml round bottomed flask fitted with a condenser and nitrogen flask. The HPLC chromatographic profile in the selected solvent system was established at time t=0 by aliquot sampling. The flask was then placed in an oil bath at 85° C., and the rate of hydrolysis was followed at 10 minutes, 30 minutes, and 45 minutes. By the time allbut 2.1% of starting material had been converted to a more polar product ($R_T$=4.58 minutes) which represented 75.6% of the mixture. 2 ml of water was added and the methanol was removed by rotary evaporation at room temperature. The aqueous solution was neutralized with 2 ml of 5% sodium bicarbonate solution. A white precipitate formed and was filtered off. Crystallization of the solid from ethanol yielded (76.7%) a fluffy white solid (280 mg).

Analysis: $^1$H NMR in $CD_3OD$ 2.54 ppm (3H, s), 3.77 ppm (3H, s), 7.3 ppm (4H, s), HPLC $R_T$=4.44 min. (77.5%) m.p. +300°C.

REACTION NO. 3

Hydrolysis of (−)methyl ester of reaction No. 2

0.18 g (0.4 mmole) of the methyl ester obtained in reaction No. 2 was dissolved in 1 ml of 2N hydrochloric acid in a reacti-vial, which was then sealed under nitrogen, and heated at 86° C. The rate of hydrolysis was followed by HPLC at 30 minutes, 1 hour and 18 hours. After this time, most (2.5% remaining) of the methyl ester had been converted to a major (91.2%) product eluting at $R_T$=5.17 minutes. The solution was adjusted to a pH of approximately 7 by addition of 5% sodium bicarbonate solution, and the solvent was removed by lyophilization. The crude solid was rinsed several times with ice cold methanol, and then filtered. The filtrate was evaporated to dryness. The solid residue was crystallized from methanol:water (1:1 by volume) and collected as a white solid (150 mg, 85.2% yield).

Analysis: $^1$H NMR in $CD_3OD$ 2.50 ppm (3H, s), 3.48 ppm (3H, m), 5.33 ppm (2H, a, J=13 Hz), 7.28 ppm (4H, s), $^{13}$C NMR in $CD_3OD$ 19.39 ppm ($CH_3$), 104.9 ppm (C-1'), M.S. m+/z 261, HPLC $R_T$=12.78 min. (98.5%), m.p. 247°-248° C.

REACTION NO. 4

Synthesis of (−)-1,3-dihydro-6-methyl-3-p-chlorophenyl-7-hydroxy-furo[3,4-c]pyridine 0.14 g (0.4 mmole) of the compound obtained in reaction No. 3 was placed in a 25 ml round bottomed flask fitted with a condenser and nitrogen flush. The solid was dissolved in 1 ml of 6N hydrochloric acid. The solution was heated at 85° C. for 1½ hours, and then cooled in an ice bath. 5% sodium bicarbonate solution was added to neutrality. The heterogeneous mixture was stripped to dryness on a rotary evaporator, and the solid residue was rinsed several times with methanol. After removing most of the methanol, the solution was spotted onto a 2000 μ silica prep TLC plate and eluted with dichloromethane:methanol (5:1 by volume). The major UV band at Rf=0.65 was removed. The organic material was rinsed free of silica with methanol, and the filtrate was stripped to dryness.

The recovered white solid (0.1 g, 96%) was found to co-elute with authentic 1,3-dihydro-6-methyl-3-p-chlorophenyl-7-hydroxy-furo[3,4-c]pyridine by HPLC.

Analysis: $^1$H NMR in $CDCl_3/CD_3OD$ 2.46 ppm (3H, s), 5.21 ppm (2H, q, J 12Hz), 6.16 ppm (1H, s), 7.31 ppm (4H, s), 7.560 ppm (1H, s), $[\delta]_D^{26}$=−109.4° (C=73 in methanol).

REACTION NO. 5

Synthesis of desacetylated form of (+)methyl ester compound of reaction No. 1

0.5 g (0.8 mmole) of the (+)methyl ester tri-acetate obtained in reaction No. 1 was dissolved in 5 ml of 1.5 N methanolic hydrogen chloride. The solution was placed in a 5 ml round bottomed flask fitted with a condensor and nitrogen flask.

The HPLC chromatographic profile in the selected solvent system was established at time t=0 by aliquot sampling. The flask was then placed in an oil bath at 85° C., and the rate of hydrolysis was followed at t=20 minutes, 40 minutes and 60 minutes. Total consumption of the starting material was observed in this time, and a major product (86.7%) was found at $R_T$=5.74 minutes. 2 ml of water was added and the methanol was removed by rotary evaporation at room temperature. The aqueous solution was neutralised with 2 ml of 5% sodium bicarbonate solution. The white solid (340 mg) which formed was collected (yield=93.2%).

Analysis: $^1$H NMR in $CD_3OD/CDCl_3$, 2.54 ppm (3H, s), 3.76 ppm (3H, s), 5.40 ppm (2H, a, j=102 Hz), 7.29 ppm (4H, s).

REACTION NO. 6

Hydrolysis of the (+)methyl ester of reaction No. 5

Without purification, the whole (340 mg, 0.74 mmole) of the product obtained in reaction No. 5 was placed in a reacti-vial with 1 ml of 2N hydrochloric acid. The reacti-vial was sealed under nitrogen, and heated at 85° C. for 18 hours. The solution was then cooled and 5% sodium bicarbonate solution was added to adjust the pH to approximately 7. The solvent was removed by lyophilization. The crude solid was rinsed several times with ice cold methanol, and was then filtered. The filtrate was stripped to dryness. The solid residue was crystallised form methanol:water 4:1 by volume, and the resultant white solid (180 mg, 58.4% yield) was collected.

Analysis: $^1$H NMR in $CD_3OD$ 2.56 ppm (3H, s), 3.55 ppm (3H, m), 5.48 ppm (2H, s), 6.16 ppm (1H, s), 7.34 ppm (4H, s); $^{13}$C NMR in $CD_3OD$ 19.56 ppm ($CH_3$), 105.21 ppm (C-1'); M.S. m+/z 261 ; HPLC m.p. 259°-261° C.

REACTION NO. 7

Synthesis of (+)-1,3-dihydro-6-methyl-3-p-chlorophenyl-7-hydroxy-furo[3,4-c]pyridine 0.17 g (0.38 mmole) of the compound obtained in reaction No. 6 was placed in a 10 ml round bottomed flask fitted with a condenser and nitrogen flask. The solid was dissolved in 1 ml of 6N hydrochloric acid. The solution was heated at 85½ C. for 1½ hours, and then cooled in an ice bath. 5% sodium bicarbonate solution was added until neutrality. The heterogeneous mixture was stripped to dryness on a rotary evacuator, and the solid residue was rinsed several times with methanol. After removing most of the methanol, the solution was spotted onto a 2000 μ silica prep TLC plate and eluted with dichloromethane:methanol (5:1 by volume). The major UV band at Rf=0.65 was removed. The organic material was rinsed free of silica with methanol, and the filtrate was stripped to dryness. The recovered white solid (70 mg, 70.5% yield) co-eluted with authentic 1,3-dihydro-6-methyl-3-p-chloromethyl-7-hydroxyfuro[3,4-c]pyridine on TLC and had an identical retention time to authentic 1,3-dihydro-6-methyl-3-p-chlorophenyl-7-hydroxyfuro[3,4-c]pyridine by HPLC.

Analysis: $[\delta]_D^{26} = +117.3$. (C=4.67 in methanol).

EXAMPLE 2

This example describes the separation of the stereoisomers of 1,3-dihydro-6-methyl-3-isopropyl-7-hydroxy-furo[3,4-c] pyridine (I:$R_3$=(CH$_3$)$_2$CH $R_4$=H $R_6$=CH$_3$) with (D-tetraacetateglucosyl) bromide.

REACTION NO. 1

Synthesis of (+) and (−)-1,3-dihydro-6-methyl-3-isopropylfuro[3,4-c]pyridine 7-O-(D-tetraacetate-glucosyl)

The reaction of (tetra-O-acetyl-glucosyl) bromide on the 1,3-dihydro-6-methyl-3-isopropyl-7-hydroxy-furo[3,4-c]pyridine, is carried out in the same condition as described in reaction No. 1 of the example 1, but without selective crystallization, because the difference of solubility in alcoholic medium, of the (+) and the (−) forms of the resulting compound, is not sufficient.

REACTION NO. 2

Deacetylation of 1,3-dihydro-6-methyl-3-isopropyl-furo[3,4-c]pyridine-7-O-(D-tetracetate-glucosyl) and separation of the deacetylated diastereomers In a 100 ml-erlen, were poured 6 g (12.4 mmole) of the 1,3-dihydro-6-methyl-3-isopropyl-7-O-(D-tetraacetate-glucosyl)-furo[3,4-c]pyridine, and 50 ml of methanol. The mixture was cooled with ice to 10° C, then saturated with ammonia. The mixture was then allowed to rest overnight in refrigerator. After filtration, the obtained precipitate was washed with methanol, then with diethyl-ether. The compound was then treated with 160 ml of a mixture of ethanol:water (50:50 by volume). 1.3 g of white solid were filtered off. The filtrate was concentrated and provided a second solid which was recrystallised in ethanol. After filtration, there was obtained 1.4 g of a crystalline solid (overall yield:67%).

Based on spectroscopic evaluation, the first solid was determined to be the (−) and the second solid the (+) of 1,3-dihydro-6-methyl-3-isopropyl-7-O-(D-glucosyl) furo[3,4-c]pyridine.

REACTION NO. 3

Synthesis of the (+)-1,3-dihydro-6-methyl-3-isopropyl-7-hydroxy-furo[3,4-c]pyridine In a 50 ml-erlen were poured 0.57 g (1.6 mmole) of the (+) compound obtained in the above reaction, 3 ml of a 6N chlorhydric acid solution and 1 ml of water. The mixture was warmed to 80° C. for about two hours, then cooled at room temperature. The obtained precipitate was filtrated off, then washed with water and dissolution of the precipitate occurs. Thereafter, the washing-waters were neutralized with sodium bicarbonate and precipitation occurs. The precipitate was then washed with water and dried to yield 0.20 g (65%) of the title compound.

We claim:

1. A method for the separation of stereoisomers of 7-hydroxy-furo[3,4-c]pyridine derivatives of the formula

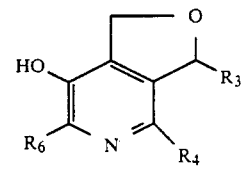

wherein $R_3$ represents a hydrogen atom, a straight chain saturated hydrocarbon group having from 1 to 5 carbon atoms or unsaturated hydrocarbon group having from 2 to 5 carbon atoms, a heterocyclic group having up to 6 ring atoms, a phenyl group, a phenylalkyl or phenylalkenyl group, said groups being optionally substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α or β-alkoxy-N-pyrrolidinyl groups in which the alkoxy group has from 1 to 5 carbon atoms; $R_4$ represents a hydrogen or chlorine atom and $R_6$ represents a lower saturated or unsaturated hydrocarbon group up to $C_5$, optionally substituted by a hydroxy radical, by a amino rest N(R)$_2$ wherein R stands for hydrogen or a lower alkyl up to $C_3$, which comprises:

reacting a fully O-acetylated monosaccharide halogenide with a racemate of the selected 7-hydroxyfuro[3,4-c] pyridine derivative to form the (+) and (−) (O-acetylated monosaccharide) (furo[3,4-c]pyridine 7-yl derivative) ethers, then separating the (+) and the (−) ethers by selective crystallization, in a hydroalcoholic medium, either of the acetylated forms or of the corresponding desacetylated forms and, finally, working up each of the separated derivatives, optionally hydrolysing the ester function, and breaking the ether bond between monosaccharide and furo[3,4-c] pyridine derivative.

2. The method of claim 1 wherein the desacetylation is performed before the selective crystallization.

3. The method of claim 1 wherein the selective crystallization is performed before the desacetylation.

4. The method of claim 2 or 3 wherein the selective crystallization is performed in an aqueous solution of a lower alkanol selected from the group consisting of methanol, ethanol and the propanols.

5. The method of claim 1 wherein the monosaccharide halogenide is a bromide of glycoside, chloride of glycoside, a bromide of glucuronate-ester or a chloride of glucuronate-ester.

* * * * *